United States Patent
Doering

(10) Patent No.: US 10,881,595 B2
(45) Date of Patent: Jan. 5, 2021

(54) ANHYDROUS ANTIPERSPIRANT SUSPENSIONS HAVING IMPROVED STABILITY

(71) Applicant: Henkel AG & Co. KGaA, Duesseldorf (DE)

(72) Inventor: Thomas Doering, Dormagen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/299,543

(22) Filed: Mar. 12, 2019

(65) Prior Publication Data

US 2019/0282470 A1    Sep. 19, 2019

(30) Foreign Application Priority Data

Mar. 13, 2018 (DE) .................. 10 2018 203 780

(51) Int. Cl.

| | |
|---|---|
| *A61K 8/26* | (2006.01) |
| *A61K 8/25* | (2006.01) |
| *A61Q 15/00* | (2006.01) |
| *A61K 8/92* | (2006.01) |
| *A61K 8/28* | (2006.01) |
| *A61K 8/9794* | (2017.01) |
| *A61K 8/58* | (2006.01) |
| *A61K 8/73* | (2006.01) |
| *A61K 8/04* | (2006.01) |

(52) U.S. Cl.
CPC ............... *A61K 8/26* (2013.01); *A61K 8/044* (2013.01); *A61K 8/25* (2013.01); *A61K 8/28* (2013.01); *A61K 8/585* (2013.01); *A61K 8/732* (2013.01); *A61K 8/92* (2013.01); *A61K 8/9794* (2017.08); *A61Q 15/00* (2013.01); *A61K 2800/874* (2013.01)

(58) Field of Classification Search
None
See application file for complete search history.

(56) References Cited

U.S. PATENT DOCUMENTS

| | | | |
|---|---|---|---|
| 4,526,780 A | 7/1985 | Marschner et al. | |
| 6,849,251 B2* | 2/2005 | Banowski | A61K 8/26 424/400 |
| 8,828,367 B2* | 9/2014 | Banowski | A61K 8/0229 424/401 |
| 10,076,482 B2 | 9/2018 | Auburn et al. | |
| 2019/0183743 A1 | 6/2019 | Doering et al. | |
| 2019/0183753 A1 | 6/2019 | Doering et al. | |
| 2019/0282470 A1 | 9/2019 | Doering | |

FOREIGN PATENT DOCUMENTS

| | | |
|---|---|---|
| DE | 102018203780 A1 | 9/2019 |
| EP | 1393712 A2 | 3/2004 |
| FR | 3002140 A1 | 8/2014 |
| GB | 2096891 A | 10/1982 |

OTHER PUBLICATIONS

English translation of "Description" of EP 1 393 712 A2. (Year: 2004).*
English translation of claims of EP 1 393 712 A2. (Year: 2004).*
Dr. Juergen Falbe, et al.: "Roempp Chemie Lexikon", 10th Edition, pp. 4585-4586, printed in Germany, 1999.

* cited by examiner

*Primary Examiner* — Sin J Lee
(74) *Attorney, Agent, or Firm* — Lorenz & Kopf, LLP

(57) ABSTRACT

The present disclosure relates to an antiperspirant composition for a roll-on application comprising a) at least one antiperspirant active substance including an inorganic or organic salt of aluminum, zirconium or a mixture thereof, b) a rice starch and c) a hydrophobically modified clay mineral. Furthermore, the present disclosure relates to a roll-on applicator including a composition as contemplated herein, and a non-therapeutic use of a composition as contemplated herein.

8 Claims, No Drawings

ANHYDROUS ANTIPERSPIRANT SUSPENSIONS HAVING IMPROVED STABILITY

CROSS-REFERENCE TO RELATED APPLICATION

This application claims priority to German Patent Application No. 10 2018 203 780.9, filed Mar. 13, 2018, which is incorporated herein by reference in its entirety.

TECHNICAL FIELD

The present disclosure relates to an antiperspirant composition for a roll-on application, wherein the composition is advantageously applicable in roll-on applicators. Furthermore, the present disclosure relates to a roll-on applicator comprising a composition as contemplated herein, and a non-therapeutic use of a composition as contemplated herein.

BACKGROUND

The washing, cleaning and care of one's own body represents a basic human need. The manufacturers of personal hygiene products are constantly trying to meet these needs of people in many ways. Especially important for daily hygiene is the prolonged elimination or at least reduction of body odor. Numerous specific deodorant personal care products are known in the art which have been developed for use in body regions having a high density of sweat glands, in particular in the axillary region and on the feet.

Body odor arises to a large extent from the bacterial decomposition of individual components of sweat on the skin. In body deodorization, one can roughly differentiate between active substances which absorb (zinc ricinoleate, cyclodextrins, ion exchangers) or cover up (fragrances, perfumes) unpleasant-smelling substances already formed, and active substances which prevent, or at least slow down the decomposition of sweat and the formation of unpleasant-smelling substances (germ-inhibiting active substances, prebiotic components and enzyme inhibitors). Depending on the chosen mechanism by which body odor is to be prevented, odor absorbers, fragrances, deodorizing ion exchangers, germ-inhibiting agents, prebiotic components and enzyme inhibitors can be used as cosmetic deodorizing active substances. The active substances must be present in the compositions, wherein it must be ensured that the composition can be applied to the skin and the antiperspirant active substance reaches its site of action. At the same time, the compositions should be able to be conveniently provided in a desired dosage form and the compositions should not cause an unpleasant sensation on the skin.

The compositions can be packaged in different dosage forms, for example, as powder, in stick form, as an aerosol spray, pump spray, liquid and gel roll-on application, cream, gel and as a soaked flexible substrate (towels). The dosage form determines the form and ingredients of the compositions. For example, when the composition is provided as a powder, its ingredients must form a free flowing solid; for example, when the composition is provided as a stick, it should form a viscous composition that has a creamy texture; and, for example, when the dosage form is an aerosol spray or a pump spray, certain antiperspirant active substances must not be used. The development of the desired dosage forms must take into account the corresponding boundary conditions.

A very popular dosage form for consumers is that of the roll-on deodorant, also called roll-on applicator. In this dosage form, a known antiperspirant composition is found in a container which is provided with a ball which can be brought into contact with the antiperspirant composition inside the container, wherein by forced rotation of the ball, a film located on the surface of the ball, the film including the antiperspirant composition, can be passed through a gap between the ball and container past the outside of the roll-on applicator, whereby the antiperspirant composition can be applied from there.

In known compositions which are used in roll-on applicators as a dosage form, particulate salts comprising aluminum and/or zirconium are used as highly effective substances for deodorant and antiperspirant activity. The known compositions in the roll-on applicators thus represent suspensions. However, suspensions are afflicted with disadvantages that affect their stability. The solids in the compositions can settle so that the user must shake the roll-on applicator before use to ensure a homogeneous distribution of the ingredients. In addition, the fluids segregated after sedimentation and/or syneresis, in particular the silicone oil frequently used in these compositions, are very thin and, in the lateral position or headstand of the roll-on applicator, pass through the gap between the ball and the housing. This leakage problem could not be solved satisfactorily so far.

BRIEF SUMMARY

This disclosure provides an antiperspirant composition for a roll-on application, including at least one antiperspirant active substance including an inorganic or organic salt of aluminum, zirconium or a mixture thereof, a rice starch and a hydrophobically modified clay mineral. This disclosure also provides a roll-on applicator including a device with ball and housing and the aforementioned composition.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object underlying the present disclosure is to provide an antiperspirant composition which is particularly well suited for use in a roll-on applicator. In particular, it was an object of the present disclosure to provide an antiperspirant composition which, when used in a roll-on applicator, shows no tendency to leak or at least a reduced tendency to leak.

The problem underlying the present disclosure is solved by the subject matter of the instant disclosure. A first subject of the present disclosure is therefore an antiperspirant composition for a roll-on application comprising a) at least one antiperspirant active substance comprising an inorganic or organic salt of aluminum, zirconium or a mixture thereof, b) a rice starch and c) a hydrophobically modified clay mineral.

Surprisingly, it has been found that this composition minimizes the leakage problem that roll-on applicators stick. The advantage associated with the composition of the present disclosure is also due to a more stable suspension. The antiperspirant composition according to the present disclosure shows less tendency for the solid components to sink and less tendency for syneresis. In addition, the rheological behavior is partly responsible for the beneficial properties that are associated with the antiperspirant composition. It is thus particularly advantageous for use in roll-on applicators.

A roll-on application is to be understood to mean any application for the prevention of body odors that makes use of a roll-on applicator. A roll-on applicator is to be understood to mean any device which has a housing and a ball via which the release of the antiperspirant composition takes place. The term "roll-on applicator" is used synonymously with the term "roll-on deodorant".

The antiperspirant composition comprises an antiperspirant active substance comprising an inorganic or organic salt of aluminum and/or zirconium. This means that an inorganic or organic salt of aluminum and/or an inorganic or organic salt of zirconium is contained in the antiperspirant composition. Further, alternatively, inorganic or organic salts of mixtures of aluminum or zirconium can be contained in the antiperspirant composition. The antiperspirant active substances have no direct influence on the activity of the sweat glands, but rather minimize the sweat secretion by narrowing the discharge channels. In this case, the Al, Zr salts cause sweat inhibition on the treated skin surfaces by superficial blockage of the sweat gland ducts as a result of metal-mucopolysaccharide precipitation.

The term "rice starch" is to be understood to mean any starch that is obtained from rice. Starch is a reserve carbohydrate, which is stored by many plants in the form of starch grains (granules), which are usually from about 1 to about 200 μm in size, in various parts of plants, for example, in tubers or roots, grain seeds, fruits and in the marrow. Starch belongs to the family of homoglycans and is a polycondensation product of D-glucose. In this case, starch includes three structurally different polymers of D-glucopyranose, namely the amylose, the amylopectin and a so-called intermediate fraction. Higher plants contain 0 to about 45% by weight amylose, based on the dry matter. The intermediate fraction, also referred to as abnormal amylopectin, is structurally between the amylose and the amylopectin.

Amylose includes predominantly linear α-1,4-glycosidically linked D-glucose, $M_w$ from about 50,000 to about 150,000. The resulting chains form double helices in the starches. In addition to the α-1,4 linkages described for amylose, amylopectin also contains α-1,6 bonds as branching sites in an amount from about 4 to about 6%. The average distance between the branching sites is from about 12 to about 17 glucose units. The molecular weight of $10^7$ to $7 \times 10^8$ corresponds to about $10^5$ glucose units, making amylopectin one of the largest biopolymers. The branches are distributed over the molecule such that a tuft structure having relatively short side chains develops.

In addition to the linkage and the associated amylopectin and amylose content, and in addition to the molecular weight, the macroscopic structure of the particles also plays an important role in the properties of the starch. The origin of the starch essentially determines the size, size distribution and shape of the starch grains. From the above chemical and structural differences, properties result that make the selected rice starch particularly suitable for the particular application.

As can be seen from the examples, the best results are achieved when the rice starch (b) is derived from the plant species *Oryza sativa*. Starch derived from this species surprisingly shows the best results. The properties of structure, chemical composition, size and/or size distribution of starch grains appear to display particularly advantageous effects with this starch. Thus, in a particularly advantageous preferred embodiment of the present disclosure, the antiperspirant composition according to the present disclosure comprises rice starch that is derived from *Oryza sativa* rice starch.

According to a further preferred embodiment of the present disclosure, the rice starch (b) is present in the antiperspirant composition as a powder treated with a cationic surfactant, wherein more preferably the amount of the cationic surfactant is from about 0.01 to about 1% by weight, more preferably from about 0.03 to about 0.3% by weight, based on the weight of the treated rice starch. The quantities are based on the amounts by weight used in the production of the treated rice starch. For example, for about 1% by weight treated rice starch, about 1 part by weight of cationic surfactant is treated with about 99 parts by weight of rice starch.

The production of the treated rice starch can of course also be carried out in a suspension. Preferred cationic surfactants are alkyl ammonium halides in which at least one alkyl group comprises of from about 8 to about 24 C atoms, more preferably from about 10 to about 20 C atoms, most preferably from about 14 to about 18 C atoms. For example, preferred rice starches are treated with cetrimonium chloride.

A commercially available rice starch with which advantageous effects could be detected is the rice starch D.S.A. 7 of Agrana AG.

In a preferred embodiment of the present disclosure, the rice starch (b) in the antiperspirant composition is contained in an amount from about 0.1 to about 10% by weight, preferably from about 0.2 to about 5% by weight, more preferably from about 0.4 to about 2% by weight, based on the total weight of the antiperspirant composition. The rice starch is advantageously effective in these quantitative ranges. The preferred quantitative ranges are based on rice starch and treated rice starch.

The term "clay mineral" is to be understood in the context of the present application as usual in the specialist literature. In this regard, reference is made to the definition in accordance with Rompp ("Rompp Lexikon Chemie", J. Falbe, M. Regitz (Ed.), 10th Edition, Thieme-Verlag). Accordingly, clay minerals belong predominantly to the phyllosilicates, also called sheet silicates, but also to the band silicates. The structure of sheet silicates can be described by layers of $SiO_4$ tetrahedrons bonded to silicate tetrahedral layers. The tetrahedral layers are linked to octahedral layers, wherein the octahedra have different metals, in particular Al, Mg, Fe, in the center. Depending on the valency of the metals in the center of the octahedral layer (in part also the tetrahedral layer, when not Si is not located in the center of the tetrahedron), monovalent or divalent ions are balanced at the surface of the octahedral layer (or the tetrahedral layer) for external neutrality. Water can also penetrate between the layers in some clay minerals, so that such clay minerals are swellable. The tetrahedral layer and the octahedral layer alternate along the C-axis of the crystal. A sequence in which a tetrahedral layer always follows an octahedral layer is regarded as a two-layer clay mineral; an octahedron layer between two tetrahedral layers is regarded as a three-layer clay mineral.

According to a preferred embodiment of the present disclosure, the clay mineral is a phyllosilicate, that is, the hydrophobically modified clay mineral is preferably a hydrophobically modified phyllosilicate. More preferably, the hydrophobically modified phyllosilicate is a hydrophobically modified three-layer silicate, more preferably a swellable hydrophobically modified three-layer silicate.

Hydrophobically modified clay minerals are understood to mean clay minerals whose naturally occurring metal cations are completely or partially replaced by cations substituted by hydrophobic groups, preferably ammonium cations substituted by long-chain alkyl groups, wherein the long-chain alkyl groups preferably include from about 5 to about 30, particularly preferably from about 7 to about 25, very preferably from about 10 to about 20 carbon atoms. The advantage of the hydrophobically modified clay minerals lies in the compatibility with organic solvents.

The production of the hydrophobically modified clay minerals includes any clay minerals contacting salts comprising cations having hydrophobic groups. For example, clay minerals can be suspended in a liquid medium in which cations having hydrophobic groups are present dissolved, wherein the liquid phase is separated after contacting and the thus hydrophobized clay minerals are dried.

According to a preferred embodiment of the present disclosure, the hydrophobically modified clay mineral (c) is a hydrophobically modified phyllosilicate, more preferably a hydrophobically modified kaolinite, a hydrophobically modified hectorite, a hydrophobically modified halloysite, a hydrophobically modified illite, a hydrophobically modified beidellite, a hydrophobically modified nontronite, a hydrophobically modified saponite, a hydrophobically modified smectite, a hydrophobically modified montmorillonite or a hydrophobically modified bentonite. Especially advantageous is the use of a hydrophobically modified bentonite in the antiperspirant composition as contemplated herein.

It has been confirmed experimentally that the choice of the phyllosilicate has a significant influence on the stability properties of the antiperspirant composition as contemplated herein. In particular, bentonite has advantageous effects in the antiperspirant composition. Bentonite is a clay mineral that contains montmorillonite as its main constituent. This significantly influences the swelling behavior of the clay mineral.

The fluid-mechanical properties of clay minerals are influenced by the content of montmorillonite. Preferably, a bentonite is used which contains more than about 50%, preferably more than about 60%, more preferably more than about 70%, even more preferably more than about 80% montmorillonite. A suitable commercially available clay mineral for use in the composition as contemplated herein is the product Bentone 38 V CG.

According to further preferred embodiment of the present disclosure, the antiperspirant composition comprises the hydrophobically modified clay mineral (c) in an amount from about 1 to about 10% by weight, preferably from about 1.5 to about 7.5% by weight, more preferably from about 2 to about 5% by weight, based on the total weight of the antiperspirant composition. The hydrophobically modified clay mineral is particularly advantageous in these quantitative ranges.

The composition as contemplated herein, in particular a composition comprising hydrophobically bentonite with rice starch that is derived from the *Oryza sativa* plant species, is surprisingly suitable for minimizing the problem of leakage underlying the present disclosure. An obvious starting point for finding a solution to the problem underlying the present disclosure would be initially constructive, that is, it would be quite obvious to change the arrangement of the ball in the housing in a certain way or to optimize the shape of the ball bed, so that the emission of segregated liquids from the roll-on applicator is minimized. However, constructive measures cannot usually solve the problem satisfactorily. On the one hand, the gap between the ball and the housing must be sufficiently wide so that a sufficiently thick film is guided out of the housing; on the other hand, the gap must not be too wide in order to prevent the leakage problem from being promoted. That an antiperspirant composition can be developed to minimize or suppress the leakage problem can in itself be considered as surprising.

The best results for solving the object underlying the present disclosure have been achieved by antiperspirant compositions which comprise the at least one antiperspirant active substance comprising an inorganic or organic salt of aluminum, zirconium or a mixture thereof, a rice starch derived from the *Oryza sativa* plant species, and a hydrophobically modified bentonite. This is unpredictable in the sense that both types of starch and clay minerals have a variety of parameters that can be changed to influence and enhance properties of compositions.

According to a preferred embodiment of the present disclosure, the antiperspirant active (a) is water-soluble. According to a further preferred embodiment of the present disclosure, the antiperspirant active substance (a) is selected from an aluminum chlorohydrate, preferably aluminum sesquichlorohydrate, aluminum chlorohydrex propylene glycol (PG), aluminum chlorohydrex polyethylene glycol (PEG), aluminum sesquichlorohydrex PG, aluminum sesquichlorohydrex PEG, aluminum PG dichlorohydrex, aluminum PEG-dichlorhydrex or aluminum hydroxide; or is selected from an aluminum zirconium chlorohydrate, preferably aluminum zirconium trichlorohydrate, aluminum zirconium tetrachlorohydrate, aluminum zirconium pentachlorohydrate or aluminum zirconium octachlorohydrate; or is selected from an aluminum zirconium chlorohydrate glycine complex, more preferably aluminum zirconium trichlorohydrex glycine, aluminum zirconium tetrachlorohydrex glycine, aluminum zirconium pentachlorohydrex glycine, aluminum zirconium octachlorohydrex glycine, or is selected from sodium aluminum chlorohydroxyacetate, aluminum bromohydrate or aluminum chloride. Further preferred antiperspirant active substances are selected from aluminum chlorohydrate, in particular aluminum chlorohydrate having the general formula $[Al_2(OH)_5Cl.1\text{-}6H_2O]_n$, more preferably $[Al_2(OH)_5Cl.2\text{-}3H_2O]_n$, which can be present in inactivated or in activated (depolymerized) form, and aluminum chlorohydrate having the general formula $[Al_2(OH)_4Cl_2.1\text{-}6H_2O]_n$, preferably $[Al_2(OH)_4Cl_2\ 2\text{-}3H_2O]_n$, which can be present in inactivated or in activated (depolymerized) form. Examples of commercially available products are the series AAZG from Summit Reheis, in particular aluminum zirconium pentachlorohydrex (AAZG 3108).

As contemplated herein, particularly preferred antiperspirant active substances are selected from so-called "activated" aluminum salts, which are also referred to as "antiperspirant active substances" having enhanced activity. Such active substances are known in the art and are also commercially available. Activated aluminum salts are typically produced by heat treating a relatively dilute solution of the salt (for example, about 10% by weight salt) to increase its HPLC peak 4-to-peak 3 area ratio. The activated salt can then be dried to a powder, in particular spray-dried. For example, roller drying is also suitable in addition to spray drying.

Preferred antiperspirant active substances are primarily water-soluble substances. As is preferably described in the context of the present disclosure, the antiperspirant composition according to the present disclosure should be essentially anhydrous. In polar solvents, the water-soluble antiperspirant active substances are largely insoluble. In this way, a high concentration of antiperspirant active substances can be effective on the skin: The antiperspirant present in particulate form is applied to the skin during application, wherein the water-soluble active substance then dissolves in sweat and displays its effect. The antiperspirant effect is promoted through this mechanism. As contemplated herein, water solubility is understood to mean a solubility of at least 3% by weight at about 20° C., that is, amounts of at least about 3 g of the antiperspirant active substance are soluble in about 97 g of water at about 20° C. As contemplated herein, water solubility is understood to mean a solubility of at least about 5% by weight at about 20° C., that is, amounts of at least about 5 g of the antiperspirant active substance are soluble in about 95 g of water at about 20° C.

In compositions as contemplated herein, preferably 70 to 95% by weight of the particles have a size greater than about 10 μm, from about 80 to about 100% by weight of the particles have a size of up to about 75 μm and from about 90 to about 100% by weight of the particles have a size of up to about 125 μm, and most preferably from about 75 to about 80% by weight of the particles have a size greater than about 10 μm, from about 90 to about 100% by weight of the particles have a size of up to about 75 μm and from about 99 to about 100% by weight of the particles have a size up to about 125 μm, in each case based on the weight of the antiperspirant active substance. "Size" is understood to mean the diameter for spherical particles and for the ellipsoidal particles, the arithmetic mean of the longest axis to the shortest axis, wherein the lengths represents the projection under an optical microscope.

According to further preferred embodiment of the present disclosure, the antiperspirant active substance (a) is contained in the antiperspirant composition in an amount from about 5 to about 40% by weight, preferably from about 10 to about 35% by weight, more preferably from about 15 to about 30% by weight, most preferably from about 18 to about 23% by weight, based on the total weight of the antiperspirant composition. The antiperspirant active substance shows the best effect within these limits.

According to a preferred embodiment of the present disclosure, the antiperspirant composition d) contains at least one oil, preferably a silicone oil. The silicone oil is preferably selected from octamethylcyclotetrasiloxane, decamethylcyclopentasiloxane, dodecamethylcyclohexasiloxane, hexamethyldisiloxane, octamethyltrisiloxane, decamethyltetrasiloxane, polydimethylsiloxane having a viscosity of from about 3 to about 10 cSt, and mixtures thereof, wherein the mixtures are preferably selected from mixtures of decamethylcyclopentasiloxane and dodecamethylcyclohexasiloxane, mixtures of hexamethyldisiloxane, octamethyltrisiloxane and decamethyltetrasiloxane, wherein the silicone oil is most preferably selected from decamethylcyclopentasiloxane.

The viscosity of the polydimethylsiloxane is determined using a falling ball viscometer. Its viscosity can be determined with its aid using the DIN 53015. To simplify the determination of which polysiloxanes can be used as contemplated herein as second siloxanes in the cosmetic composition, the manufacturer's instructions serve for the viscosity of the polysiloxanes. The polysiloxanes used are all commercially available and usually classified by their viscosities as measured in Stokes.

The preferred silicone oils can generally be selected from dialkyl and alkylaryl siloxanes which have a vapor pressure of less than about 2.66 Pa (about 0.02 mm Hg) at about 20° C. and an ambient pressure of about 1013 hPa, such as octamethylcyclotetrasiloxane, decamethylcyclopentasiloxane, dodecamethylcyclohexasiloxane, dimethylpolysiloxane, low molecular weight phenyl trimethicone and methylphenylpolysiloxane, but also hexamethyldisiloxane, octamethyltrisiloxane and decamethyltetrasiloxane. In general, particularly preferred silicone oils are those which are cyclic, such as octamethylcyclotetrasiloxane, decamethylcyclopentasiloxane and dodecamethylcyclohexasiloxane, and mixtures thereof, as, for example, in the commercial products DC 244, 245, 344 and 345 from Dow Corning (vapor pressure at about 20° C. about 13-15 Pa).

Likewise particularly preferred are linear silicone oils having from about 2 to about 10 siloxane units, in particular hexamethyldisiloxane ($L_2$), octamethyltrisiloxane ($L_3$), decamethyltetrasiloxane ($L_4$) and also any two or three mixtures of $L_2$, $L_3$ and/or $L_4$, preferably those mixtures, as they are available, for example, in the commercial products DC 2-1184, Dow Corning® 200 (0.65 cSt) and Dow Corning® 200 (1.5 cSt) from Dow Corning. A further preferred volatile silicone oil is a low molecular weight phenyl trimethicone having a vapor pressure at about 20° C. of about 2000 Pa, as available, for example, from GE Bayer Silicone/Momentive under the name Baysilone Fluid PD 5.

Silicone oils are excellently suitable carrier oils for antiperspirant compositions as contemplated herein, since they give them a pleasant skin feeling and a low textile soiling. The advantageous silicone oils, however, are afflicted with the disadvantage of low viscosity. In the case of segregation of the antiperspirant composition, the problem of leakage is particularly great. The advantageous effect of the antiperspirant composition effected by using the rice starch with the hydrophobically modified clay mineral, in particular the rice starch derived from the *Oryza Sativa* plant species, with the hydrophobically modified bentonite is particularly significant when using the preferred silicone oils.

According to a further preferred embodiment of the present disclosure, the oil (d) is contained in the antiperspirant composition in an amount from about 40 to about 95% by weight, preferably from about 60 to about 85% by weight, more preferably from about 70 to about 80% by weight, based on the total weight of the antiperspirant composition. In particular, the silicone oil is contained in the antiperspirant composition in an amount from about 40 to about 95% by weight, preferably from about 60 to about 85% by weight, more preferably from about 70 to about 80% by weight, based on the total weight of the antiperspirant composition.

According to a further preferred embodiment of the present disclosure e), a non-volatile oil component is present as activator in the antiperspirant composition as contemplated herein, wherein the non-volatile oil component, under standard conditions (IUPAC, as of 2017), has a vapor pressure of less than about 10 Pa, preferably less than about 5 Pa at about 20° C. More preferably, the non-volatile oil component (s) comprises glycerol or an organic carbonate, most preferably propylene carbonate.

The non-volatile oil component, when contained in the antiperspirant composition, is contained in an amount from about 0.9 to about 4% by weight, preferably in an amount from about 1 to about 3% by weight and most preferably from about 1 to about 2% by weight, based on the total weight of the antiperspirant composition.

According to a preferred embodiment of the present disclosure, the antiperspirant composition is essentially anhydrous. "Essentially anhydrous" means as contemplated herein that the composition has a content of free water of not more than about 7% by weight, based on the total weight of the antiperspirant composition. "Free water" in the sense of the present application is water which is not present in the form of water of crystallization, water of hydration or similar molecularly bound water in the antiperspirant composition.

The content of water of crystallization, water of hydration or similar molecularly bound water which is contained in the constituents used, in particular in the antiperspirant active substances, does not represent free water in the sense of the present application. Free water is, for example, water which is added as a solvent, as a gel activator or as a solvent constituent of other active substances to the composition as contemplated herein. The antiperspirant compositions as contemplated herein contain, based on their total weight, from about 0 to about 7% by weight free water. Antiperspirant compositions preferred as contemplated herein, based on their total weight, contain from about 0 to about 6% by weight free water, preferably from about 0 to about 5% by weight, particularly preferably from about 0 to about 4% by weight, most preferably from about 0 to about 3% by weight free water. The antiperspirant compositions as contemplated herein are thus to be regarded as essentially anhydrous.

Antiperspirant compositions preferred as contemplated herein have a viscosity in the range of from about 1000 to about 3500 mPa·s, more preferably from about 1500 to about 3000 mPa·s, most preferably from about 2000 to about 2500 mPa·s, each measured with a Brookfield viscometer at about 23° C. with spindle 3 at a shear rate of about 10 revolutions per minute.

According to a preferred embodiment of the present disclosure, the antiperspirant composition comprises one or more fragrances or scents, also known synonymously as perfume. The definition of a scent in the sense of the present application corresponds to the definition customary in the art, as can be taken from the ROMPP Chemie Lexikon ("Rompp Lexikon Chemie", J. Falbe, M. Regitz (Ed.), 10th edition, Thieme Verlag). Fragrances or scents can be considered in the context of the present disclosure only as such, which, based on the total weight of the antiperspirant composition, are present in an amount of less than about 0.9% by weight in the antiperspirant composition and are completely soluble in the non-aqueous medium, that is, the oil. Examples of fragrance and scent compounds of the ester type are benzyl acetate, phenoxyethyl isobutyrate, p-tert-butylcyclohexyl acetate, linalyl acetate, dimethylbenzylcarbinylacetate (DMBCA), phenylethyl acetate, benzyl acetate, ethylmethylphenylglycinate, allylcyclohexylpropionate, styrallylpropionate, benzylsalicylate, cyclohexylsalicylate, floramate, melusate and jasmecyclate. Examples of fragrance and scent compounds of the ether type are benzyl ethyl ether and ambroxane, examples of fragrance and scent compounds of the aldehyde type are the linear alkanals having from about 8 to about 18 carbon atoms, citral, citronellal, citronellyloxy-acetaldehyde, cyclamen aldehyde, lilial and bourgeonal, examples of fragrance and scent compounds of the ketone type are the ionones, alpha-isomethylionone and methyl cedryl ketone, examples of fragrance and scent compounds of the alcohol type are anethole, citronellol, eugenol, geraniol, linalool, phenylethyl alcohol and terpineol, examples of fragrance and scent compounds of the terpene type are limonene and pinene. Examples of fragrance and scent compounds are pine oil, citrus oil, jasmine oil, patchouly oil, rose oil, ylang-ylang oil, muscat sage oil, chamomile oil, clove oil, mint oil, cinnamon leaf oil, lime blossom oil, juniper berry oil, vetiver oil, olibanum oil, galbanum oil, labdanum oil, orange blossom oil, neroli oil, orange peel oil and sandalwood oil, further the essential oils such as angelica root oil, aniseed oil, arnica blossom oil, basil oil, bay oil, bergamot oil, champacilla oil, silver fir oil, silver fir cone oil, elemi oil, eucalyptus oil, fennel oil, pine needle oil, geranium oil, ginger grass oil, guaiac wood oil, gurdyal balm oil, helichrysum oil, ho oil, ginger oil, iris oil, cajeput oil, calamus oil, chamomile oil, camphor oil, kanga oil, cardamom oil, cassia oil, pine needle oil, copaiba balsam oil, coriander oil, spearmint oil, caraway oil, cumin oil, lavender oil, lemon grass oil, lime oil, tangerine oil, lemon balm oil, musk kernel oil, myrrh oil, clove oil, niaouli oil, orange oil, origanum oil, palmarosa oil, patchouli oil, Peruvian balsam oil, petitgrain oil, pepper oil, peppermint oil, pimento oil, pine oil, rose oil, rosemary oil, sandalwood oil, celery oil, spik oil, star aniseed oil, turpentine oil, thuja oil, thyme oil, verbena oil, juniper berry oil, wormwood oil, wintergreen oil, hyssop oil, cinnamon oil, citronella oil, lemon oil and cypress oil. Further fragrance and scent compounds are ambrettolide, alpha-amylcinnamaldehyde, anethole, anisaldehyde, anisalcohol, anisole, methyl anthranilate, acetophenone, benzylacetone, benzaldehyde, ethyl benzoate, benzophenone, benzyl alcohol, benzyl acetate, benzyl benzoate, benzyl formate, benzyl valerate, borneol, bornyl acetate, alpha-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, hepticarboxylic acid methyl ester, heptaldehyde, hydroquinone dimethyl ether, hydroxycinnamaldehyde, hydroxycinnamyl alcohol, indole, iron, isoeugenol, isoeugenol methyl ether, isosafrole, jasmon, camphor, carvacrol, carvone, p-cresol methyl ether, coumarin, p-methoxyacetophenone, methyl-n-amyl ketone, methyl anthranilate, p-methylacetophenone, methylchavikole, p-methylquinoline, methyl-beta-naphthyl ketone, methyl-n-nonylacetaldehyde, methyl-n-nonyl ketone, muscone, beta-naphthol ethyl ether, beta-naphthol methyl ether, nerol, nitrobenzene, n-nonylaldehyde, nonyl alcohol, n-octylaldehyde, p-oxyacetophenone, pentadecanolide, β phenylethyl alcohol, phenylacetaldehyde dimethylacetal, phenylacetic acid, pulegone, safrole, salicylic acid isoamyl ester, salicylic acid methyl ester, salicylic acid hexyl ester, salicylic acid cyclohexyl ester, santalol, skatole, terpineol, thymine, thymol, gamma-undecalactone, vanillin, veratrumaldehyde, cinnamaldehyde, cinnamyl alcohol, cinnamic acid, cinnamic acid ethyl ester and cinnamic acid benzyl ester. Further (more volatile) scents are alkyl isothiocyanates (alkylmustard oils), butanedione, limonene, linalool, linalyl acetate and propionate, menthol, menthone, methyl-n-heptenone, phellandrene, phenylacetaldehyde, terpinyl acetate, citral and citronellal.

Furthermore, the compositions as contemplated herein can contain additional deodorant agents. Antimicrobial, antibacterial or antimicrobial substances, antioxidants or odor adsorbents can be used as deodorant active substances. Suitable antimicrobial, antibacterial or antimicrobial substances are in particular organohalogen compounds and halides, quaternary ammonium compounds and a number of plant extracts. Preference is given to halogenated phenol derivatives such as, for example, hexachlorophene or Irgasan DP 300 (triclosan, 2,4,4'-trichloro-2'-hydroxydiphenyl ether), 3,4,4'-trichlorocarbanilide, chlorhexidine (1,1'-hexamethylene-bis-[5-(4-chlorophenyl)]-biguanide), chlorhexidine gluconate, benzalkonium halides and cetylpyridinium chloride. Furthermore, sodium bicarbonate and sodium phenolsulfonate and, for example, the components of lime blossom oil can be used. Even less effective antimicrobial substances, which still have a specific effect against the gram-positive bacteria responsible for the sweat decomposition can be used as deodorant agents. Benzyl alcohol can also be used as a deodorant active substance. Further antibacterial deodorants are lantibiotics, glycoglycerolipids, sphingolipids (ceramides), sterols and other active substances that inhibit bacterial adhesion to the skin, for example, glycosidases, lipases, proteases, carbohydrates, di- and oligosaccharide fatty acid esters and alkylated monosaccharides and oligosaccharides. Preferred deodorant active substances are long-chain diols, for example, 1,2-alkane ($C_5$-$C_{18}$) diols, glycerol mono ($C_8$-$C_{18}$) fatty acid esters or, more preferably, glycerol mono ($C_6$-$C_{16}$) alkyl ethers, in particular 2-ethylhexyl glycerol ethers, which are very well tolerated by skin and mucous membranes and are active against corynebacteria, and further phenoxyethanol, phenoxyisopropanol (3-phenoxy-propan-2-ol), anisalcohol, 2-methyl-5-phenyl-pentane-1-ol, 1,1-dimethyl-3-phenyl-propan-1-ol, benzyl alcohol, 2-phenylethane-1-ol, 3-phenyl-propan-1-ol, 4-phenylbutan-1-ol, 5-phenylpentane-1-ol, 2-Benzylheptan-1-ol, 2,2-dimethyl-3-phenylpropan-1-ol, 2,2-dimethyl-3-(3'-methylphenyl)-propan-1-ol, 2-ethyl-3-phenylpropan-1-ol, 2-ethyl-3-(3'-methylphenyl)-propan-1-ol, 3-(3'-chlorophenyl)-2-ethyl-propan-1-ol, 3-(2'-chlorophenyl)-2-ethyl-propan-1-ol, 3-(4'-chlorophenyl)-2-ethyl-propan-1-ol, 3-(3',4'-dichlorophenyl)-2-ethyl-propan-1-ol, 2-ethyl-3-(2'-methylphenyl)-propan-1-ol, 2-ethyl-3-(4'-methylphenyl)-propan-1-ol, 3-(3',4'-dimethylphenyl)-2-ethyl-propan-1-ol, 2-ethyl-3-(4'-methoxyphenyl)-propan-1-ol, 3-(3',4'-dimethoxyphenyl)-2-ethyl-propan-1-ol, 2-allyl-3-phenyl-propan-1-ol and 2-n-pentyl-3-phenyl-propan-1-ol. Complex-forming substances can also support the deodorizing effect by stably complexing the oxidative catalytically active heavy metal ions (for example, iron or copper). Suitable complexing agents are, for example, the salts of ethylenediaminetetraacetic acid or nitrilotriacetic acid and the salts of 1-hydroxyethane-1,1-diphosphonic acid.

A further object of the present disclosure was to provide a roll-on applicator which shows a reduced tendency to leak.

The problem underlying the present disclosure is solved by the subject matter of this disclosure. A second subject of the present disclosure is therefore a roll-on applicator comprising a) a device with ball and housing, and b) the antiperspirant composition as contemplated herein.

A further object underlying the present disclosure is further achieved by the subject matter of this disclosure. A third subject of the present disclosure is therefore the non-therapeutic use of an antiperspirant composition as contemplated herein for the prevention of body odor, wherein the non-therapeutic use is provided preferably for a roll-on application.

Features relating to preferred embodiments of the first subject of the present disclosure, which are described above only in this regard, of course, apply mutatis mutandis to the second and third objects as features of preferred embodiments.

Very particularly preferred cosmetic agents as contemplated herein comprise at least one of the following embodiments A) to K).

A)
An antiperspirant composition for a roll-on application, comprising a) at least one antiperspirant active substance comprising an inorganic or organic salt of aluminum, zirconium or a mixture thereof, b) a rice starch derived from the *Oryza sativa* plant species, and c) a hydrophobically modified clay mineral, wherein the clay mineral is a phyllosilicate.

B)
An antiperspirant composition for a roll-on application, comprising a) at least one antiperspirant active substance comprising an inorganic or organic salt of aluminum, zirconium or a mixture thereof, b) a rice starch derived from the *Oryza sativa* plant species, and c) a hydrophobically modified bentonite.

C)
An antiperspirant composition for a roll-on application, comprising a) at least one antiperspirant active substance comprising an inorganic or organic salt of aluminum, zirconium or a mixture thereof, b) a rice starch derived from the *Oryza sativa* plant species, and c) a hydrophobically modified bentonite, wherein the weight fraction of montmorillonite in the bentonite, based on the weight of the bentonite, is about 50% and more, preferably more than about 60%, more preferably more than about 70%, most preferably more than about 80%.

D)
An antiperspirant composition for a roll-on application comprising a) at least one antiperspirant active comprising an inorganic or organic aluminum-zirconium salt, b) a rice starch derived from the *Oryza Sativa* plant species, and c) a hydrophobically-modified bentonite.

E)
An antiperspirant composition for a roll-on application, comprising a) at least one antiperspirant active substance comprising an inorganic or organic salt of aluminum, zirconium or a mixture thereof, b) a rice starch derived from the *Oryza sativa* plant species, and c) a hydrophobically modified bentonite, wherein the antiperspirant composition is essentially anhydrous.

F)
An antiperspirant composition for a roll-on application, comprising a) at least one antiperspirant active substance comprising an inorganic or organic salt of aluminum, zirconium or a mixture thereof, b) a rice starch derived from the *Oryza sativa* plant species, c) a hydrophobically modified bentonite and d) a silicone oil.

G)
An antiperspirant composition for a roll-on application, comprising a) at least one antiperspirant active substance comprising an inorganic or organic salt of aluminum, zirconium or a mixture thereof, b) a rice starch derived from the *Oryza sativa* plant species, c) a hydrophobically modified bentonite and d) a silicone oil, wherein the antiperspirant composition is essentially anhydrous.

H)
An antiperspirant composition for a roll-on application, comprising a) at least one antiperspirant active substance comprising an inorganic or organic salt of aluminum, zirconium or a mixture thereof, b) a rice starch derived from the *Oryza sativa* plant species, c) a hydrophobic ally modified bentonite, and d) a silicone oil selected from octamethylcyclotetrasiloxane, decamethylcyclopentasiloxane, dodecamethylcyclohexasiloxane, hexamethyldisiloxane, octamethyltrisiloxane, decamethyltetrasiloxane, polydimethylsiloxane having a viscosity of from about 3 to about 10 cSt, and mixtures thereof, wherein the silicone oil is most preferably selected from decamethylcyclopentasiloxane.

I)
An antiperspirant composition for a roll-on application comprising a) at least one antiperspirant active substance comprising an inorganic or organic salt of aluminum, zirconium or a mixture thereof, b) a rice starch derived from the *Oryza sativa* plant species, c) a hydrophobically modified bentonite, and d) decamethylcyclopentasiloxane, wherein the antiperspirant composition is essentially anhydrous, preferably has a water content from 0 to about 7% by weight, preferably from about 0 to about 6% by weight, more preferably from 0 to about 5% by weight, more preferably from 0 to about 4% by weight, most preferably from 0 to about 3% by weight, based on the total weight of the antiperspirant composition.

J)

An antiperspirant composition for a roll-on application comprising a) at least one antiperspirant active comprising an inorganic or organic salt of aluminum, zirconium or a mixture thereof in an amount from about 5 to about 40% by weight, preferably from about 10 to about 35% by weight, more preferably from about 15 to about 30% by weight, most preferably from about 18 to about 23% by weight, b) a rice starch derived from the *Oryza sativa* plant species in an amount from about 0.1 to about 10% by weight, preferably from about 0.2 to about 5% by weight, more preferably from about 0.4 to about 2% by weight, c) a hydrophobically modified bentonite in an amount from about 1 to about 10% by weight, preferably from about 1.5 to about 7.5% by weight, more preferably from about 2 to about 5% by weight, and (d) a silicone oil in an amount from about 40 to about 95% by weight, preferably from about 60 to about 85% by weight, more preferably from about 70 to about 80% by weight, in each case based on the total weight of the antiperspirant composition.

K)

Roll-on applicator comprising a device with ball and housing and an antiperspirant composition comprising a) at least one antiperspirant active comprising an inorganic or organic salt of aluminum, zirconium or a mixture thereof in an amount from about 5 to about 40% by weight, preferably from about 10 to about 35% by weight, more preferably from about 15 to about 30% by weight, most preferably from about 18 to about 23% by weight, b) a rice starch derived from the *Oryza sativa* plant species in an amount from about 0.1 to about 10% by weight, preferably from about 0.2 to about 5% by weight, more preferably from about 0.4 to about 2% by weight, c) a hydrophobically modified bentonite in an amount from about 1 to about 10% by weight, preferably from about 1.5 to about 7.5% by weight, more preferably from about 2 to about 5% by weight, and (d) a silicone oil in an amount from about 40 to about 95% by weight, preferably from about 60 to about 85% by weight, more preferably from about 70 to about 80% by weight, in each case based on the total weight of the antiperspirant composition.

In various embodiments, this disclosure provides:

1. An antiperspirant composition for a roll-on application, comprising
   a) at least one antiperspirant active substance comprising an inorganic or organic salt of aluminum, zirconium or a mixture thereof,
   b) a rice starch and
   c) a hydrophobically modified clay mineral.
2. The antiperspirant composition according to point 1, characterized in that the antiperspirant active substance (a) is water-soluble, and/or characterized in that the antiperspirant active substance (a) is selected from an aluminum chlorohydrate, preferably aluminum sesquichlorohydrate, aluminum chlorohydrex propylene glycol (PG), aluminum chlorohydrex polyethylene glycol (PEG), aluminum sesquichlorohydrex PG, aluminum sesquichlorohydrex PEG, aluminum PG dichlorhydrate, aluminum PEG dichlorhydrate or aluminum hydroxide; or is selected from an aluminum zirconium chlorohydrate, preferably aluminum zirconium trichlorohydrate, aluminum zirconium tetrachlorohydrate, aluminum zirconium pentachlorohydrate or aluminum zirconium octachlorohydrate; or is selected from an aluminum-zirconium-chlorohydrate-glycine complex, preferably aluminum zirconium trichlorohydrexglycine, aluminum zirconium tetrachlorohydrex glycine, aluminum zirconium pentachlorohydrex glycine, aluminum zirconium octachlorohydrex glycine, or selected from sodium aluminum chlorhydroxyacetate, aluminum bromohydrate or aluminum chloride.
3. The antiperspirant composition according to point 1 or point 2, characterized in that the antiperspirant active substance (a) is contained in the antiperspirant composition in an amount from 5 to 40% by weight, preferably 10 to 35% by weight, more preferably 15 to 30% by weight, most preferably 18 to 23% by weight, based on the total weight of the antiperspirant composition.
4. The antiperspirant composition according to one of the preceding points, characterized in that the rice starch (b) is derived from the plant species *Oryza sativa*.
5. An antiperspirant composition according to one of the preceding points, characterized in that the rice starch (b) is present as a powder treated with a cationic surfactant, wherein preferably the amount of the cationic surfactant is from 0.01 to 1% by weight, more preferably 0.03 to 0.3% by weight, based on the weight of the treated rice starch.
6. The antiperspirant composition according to one of the preceding points, characterized in that the rice starch (b) is contained in the antiperspirant composition in an amount from 0.1 to 10% by weight, preferably 0.2 to 5% by weight, more preferably 0.4 to 2% by weight, based on the total weight of the antiperspirant composition.
7. The antiperspirant composition according to one of the preceding points, characterized in that the hydrophobically modified clay mineral (c) is a hydrophobically modified phyllosilicate, preferably a hydrophobically modified kaolinite, a hydrophobically modified hectorite, a hydrophobically modified halloysite, a hydrophobically modified illite, a hydrophobically modified beidellite, a hydrophobically modified nontronite, a hydrophobically modified saponite, a hydrophobically modified smectite, a hydrophobically modified montmorillonite, a hydrophobically modified bentonite, in particular a hydrophobically modified bentonite.
8. The antiperspirant composition according to one of the preceding points, characterized in that the hydrophobically modified clay mineral (c) is contained in the antiperspirant composition in an amount from 1 to 10% by weight, preferably 1.5 to 7.5% by weight, more preferably 2 to 5% by weight, based on the total weight of the antiperspirant composition.
9. The antiperspirant composition according to one of the preceding points, characterized in that the antiperspirant composition contains
   d) at least one oil, preferably a silicone oil, more preferably characterized in that the silicone oil is selected from octamethylcyclotetrasiloxane, decamethylcyclopentasiloxane, dodecamethylcyclohexasiloxane, hexamethyldisiloxane, octamethyltrisiloxane, decamethyltetrasiloxane, polydimethylsiloxane having a viscosity of from 3 to 10 cSt, and mixtures thereof, wherein the blends are preferably selected from mixtures of decamethylcyclopentasiloxane and dodecamethylcyclohexasiloxane, mixtures hexamethyldisiloxane, octamethyltrisiloxane and decamethyltetrasiloxane, wherein the silicone oil is more preferably selected from decamethylcyclopentasiloxane.

10. The antiperspirant composition according to point 9, characterized in that the oil (d), preferably the silicone oil, is contained in the antiperspirant composition in an amount from 40 to 95% by weight, preferably 60 to 85% by weight, more preferably 70 to 80% by weight, based on the total weight of the antiperspirant composition.
11. The antiperspirant composition according to one of the preceding points, characterized in that the antiperspirant composition contains
    e) a non-volatile oil component as an activator, wherein the non-volatile oil component has a vapor pressure of less than 10 Pa, preferably less than 5 Pa at 20° C., wherein preferably the non-volatile oil component(s) contain glycerol or an organic carbonate, more preferably propylene carbonate.
12. The antiperspirant composition according to one of the preceding points, characterized in that the antiperspirant composition is essentially anhydrous, preferably has a water content from 0 to 7% by weight, preferably from 0 to 6% by weight, more preferably from 0 to 5% by weight, more preferably from 0 to 4% by weight, most preferably from 0 to 3% by weight, based on the total weight of the antiperspirant composition.
13. The antiperspirant composition according to one of the preceding points, characterized in that the antiperspirant composition is present in the form of a suspension.
14. A roll-on applicator comprising
    a) a device with ball and housing, and
    b) an antiperspirant composition according to one of points 1 to 13.
15. A non-therapeutic use of a composition according to any one of points 1 to 13 for the prevention of body odor, wherein the non-therapeutic use is preferably provided for a roll-on application.

The following examples are intended to illustrate the subject matter of the present disclosure without limiting it in any way.

EXAMPLES

The following composition can be produced by way of example:

| Composition | Z1* | Z2* | Z3* |
|---|---|---|---|
| Silicone oil [1] | 73.9 | 74.2 | 73.4 |
| Aluminum zirconium pentachlorohydrex [2] | 20.0 | 20.0 | 20.0 |
| Propylene carbonate | 1.0 | 1.0 | 1.0 |
| Clay mineral [3] | 4.1 | 4.1 | 4.1 |
| Rice starch [4] | 0.5 | 0.2 | 1.0 |
| Perfume | 0.5 | 0.5 | 0.5 |
| Total | 100.0 | 100.0 | 100.0 |

*specification in % by weight
[1] cyclopentasiloxane Xiameter 0245 fluid
[2] aluminum zirconium salt AAZG 3108 from Summit Reheis
[3] Bentone 38 V CG from Elementis
[4] *Oryza sativa* (rice) starch (rice starch D.S.A. 7 of Agrana AG.

The components listed in the following table were mixed and homogenized at 30° C. by way of example for the production of antiperspirant compositions. Each 100 ml of the preparations were stored for 24 h at room temperature in stationary cylinders. The deposition of a clear oil phase indicates an undesirable phase separation.

| Composition | V1* | V2* | V3* | V4* | E* |
|---|---|---|---|---|---|
| Silicone oil [1] | 79.0 | 74.0 | 78.0 | 75.0 | 74.0 |
| Aluminum zirconium pentachlorohydrex [2] | 20.0 | 20.0 | 20.0 | 20.0 | 20.0 |
| Clay mineral [3] | – | 4.0 | – | 4.0 | 4.0 |
| Rice starch [4] | – | – | 1.0 | – | 1.0 |
| Corn starch [5] | – | 1.0 | – | – | – |
| Propylene carbonate | 1.0 | 1.0 | 1.0 | 1.0 | 1.0 |
| Total | 100.0 | 100.0 | 100.0 | 100.0 | 100.0 |
| Stability [6] | – | +/– | +/– | +/– | + |
| Leak tightness [7] | – | – | – | – | + |

*specification in % by weight
[1] cyclopentasiloxane Xiameter 0245 fluid
[2] aluminum zirconium salt AAZG 3108 from Summit Reheis
[3] Bentone 38 V CG from Elementis
[4] *Oryza sativa* (rice) starch (rice starch D.S.A. 7 of Agrana AG.
[5] corn starch hydrolyzed corn starch octenylsuccinate
[6] The stability was assessed after 24 hours of rest in a stand cylinder. The symbol "–" stands for a complete separation of the phases; the symbol "+/–" stands for an unstable suspension in which a clear oil phase is recognizable; the symbol "+" stands for a stable suspension.
[7] The leak tightness of the roll-on applicator was assessed after a one-week standstill. The symbol "–" stands for an observed leak, while the symbol "+" stands for a leak tight roll-on applicator.

Examples V1 to V4 represent comparative examples since they contain either no clay mineral or no starch or no rice starch. Only the combination of the rice starch used in Example E as contemplated herein with Bentone 38 V CG shows an outstanding effect.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:
1. An antiperspirant composition in the form of a suspension for a roll-on application, consisting of:
    a) at least one antiperspirant active substance comprising an inorganic or organic salt of aluminum, zirconium or a mixture thereof and present in an amount of from about 18 to about 23 percent by weight based on a total weight of the antiperspirant composition,
    b) a rice starch derived from the plant species *Oryza sativa* and present in an amount of from about 0.4 to about 2 percent by weight based on a total weight of the antiperspirant composition,
    c) a hydrophobically modified hectorite present in an amount of from about 2 to about 5 percent by weight based on a total weight of the antiperspirant composition,
    d) decamethylcyclopentasiloxane present in an amount of from about 70 to about 80 percent by weight based on a total weight of the antiperspirant composition, and
    e) a non-volatile oil component present in an amount of from about 1 to about 2% by weight, based on the total weight of the antiperspirant composition, and optionally
    f) a perfume and/or an additional deodorant agent.

2. The antiperspirant composition according to claim 1, wherein said at least one antiperspirant active substance (a) is aluminum zirconium pentachlorohydrex glycine.

3. A roll-on applicator comprising
   a) a device with ball and housing, and
   b) an antiperspirant composition according to claim 1.

4. The antiperspirant composition according to claim 1, wherein said at least one antiperspirant active substance is chosen from sodium aluminum chlorhydroxyacetate, aluminum bromohydrate or aluminum chloride.

5. The antiperspirant composition according to claim 1, wherein the rice starch is present in an amount of about 1 percent by weight based on the total weight of the antiperspirant composition.

6. The antiperspirant composition according to claim 1, wherein the hydrophobically modified hectorite is present in an amount of about 4 percent by weight based on the total weight of the antiperspirant composition.

7. The antiperspirant composition according to claim 1, wherein the cyclopentasiloxane is present in an amount of about 74 percent by weight based on the total weight of the antiperspirant composition.

8. The antiperspirant composition according to claim 1, wherein the non-volatile oil is propylene carbonate and is present in an amount of about 1 percent by weight based on the total weight of the antiperspirant composition.

* * * * *